US009717722B2

(12) United States Patent
Orlow et al.

(10) Patent No.: US 9,717,722 B2
(45) Date of Patent: Aug. 1, 2017

(54) METHODS AND AGENTS FOR TREATING TYROSINASE-POSITIVE ALBINISM (71) Applicant: NEW YORK UNIVERSITY, New York, NY (US)

(72) Inventors: Seth J. Orlow, New York, NY (US); Prashiela Manga, Forest Hills, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/890,696

(22) PCT Filed: May 13, 2014

(86) PCT No.: PCT/US2014/037810
§ 371 (c)(1),
(2) Date: Nov. 12, 2015

(87) PCT Pub. No.: WO2014/186344
PCT Pub. Date: Nov. 20, 2014

(65) Prior Publication Data
US 2016/0120860 A1    May 5, 2016

Related U.S. Application Data (60) Provisional application No. 61/822,519, filed on May 13, 2013.

(51) Int. Cl.
A61K 31/44       (2006.01)
A61K 31/4706     (2006.01)
A61K 31/122      (2006.01)
A61K 31/436      (2006.01)

(52) U.S. Cl.
CPC ........ A61K 31/4706 (2013.01); A61K 31/122 (2013.01); A61K 31/436 (2013.01)

(58) Field of Classification Search
CPC .................................. A61K 31/4706
USPC ...................................... 514/291
See application file for complete search history.

(56) References Cited

U.S. PATENT DOCUMENTS

| 7,378,232 | B2 * | 5/2008 | Orlow ............... | G01N 33/5008 435/29 |
| 7,897,184 | B1 | 3/2011 | Rana et al. | |
| 8,685,472 | B2 | 4/2014 | Rana et al. | |
| 8,822,540 | B2 * | 9/2014 | Brooks ............... | A61K 8/35 514/612 |
| 2009/0298868 | A1 * | 12/2009 | Orlow ............... | A61K 31/47 514/305 |

FOREIGN PATENT DOCUMENTS

| WO | 0164206    | 9/2001 |
| WO | 2009051437 | 4/2009 |
| WO | 2011106655 | 9/2011 |

OTHER PUBLICATIONS

Komatsu Mol Pharmacol 74:1576-1586, 2008.*
Njaria et al. Expert Opin. Ther. Patents (2015) 25(9):1003-1024.*
Tanaka et al., "Topical Rapamycin Therapy is Effective for Hypomelanotic Macules Arising in Tuberous Sclerosis Complex", iPCC International Pigment Cell Conference, Sep. 21-24, 2011, France, abstract only.
Ni-Komatsu et al., "Chemical Genetic Screening Identifies Tricyclic Compounds that Decrease Cellular Melanin Content", Journal of Investigative Dermatology, 2008, 128:1236-1247.
Ni-Komatsu et al., "Identification of Quinolines that Inhibit Melanogenesis by Altering Tyrosinase Family Trafficking", Mol Pharmacol, 2008, 74:1576-1586.
Sabitha et al., "Hyperpigmentation of the Skin Following Chloroquine Treatment—Case Series Report", Iranian Journal of Pharmacology & Therapeutics, 2005, 4:70-71.
Hah et al., "Induction of Melanogenesis by Rapamycin in Human MNT-1 Melanoma Cells", Ann Dermatol, 2012, 24:151-157.
RoseMblat et al., "Melanosomal Defects in Melanocytes from Mice Lacking Expression of the Pink-Eyed Dilution Gene: Correction by Culture in the Presence of Excess Tyrosine", Experimental Cell Research, 1998, 239:344-352.
Williams et al., "Identification of Compounds that Bind Mitochondrial F1F0 ATPase by Screening a Triazine Library for Correction of Albinism", Chemistry & Biology, 2004, 11:1251-1259.
Chen et al., "Correction of Defective Early Tyrosinase Processing by Bafilomycin A1 and Monensin in Pink-Eyed Dilution Melanocytes", Pigment Cell Res, 2004, 17:36-42.
Gronskov et al., "Oculocutaneous albinism", Orphanet Journal of Rare Diseases, 2007, 2:43 (1-8).
Moriyama et al., "Rapamycin treatment causes developmental delay, pigmentation defects, and gastrointestinal malformation on Xenopus embryogenesis", Biochemical and Biophysical Research Communications, 2011, 404:974-978.
Onojafe et al., "Nitisinone improves eye and skin pigmentation defects in a mouse model of oculocutaneous albinism", The Journal of Clinical Investigation, 2011, 121:3914-3923.
Manga et al., "Informed reasoning: repositioning of nitisinone to treat oculocutaneous albinism", The Journal of Clinical Investigation, 2011, 121:3828-3831.
Kim JH et al (2015) Melanogenesis inhibition of β-lapachone, a natural product from Tabebuia avellanedae, with effective in vivo lightening potency. Arch Dermatol Res. 307(3):229-238.
Pillaiyar T et al (2015) Inhibitors of melanogenesis: a patent review (2009-2014). Expert Opin Ther Pat 25(7):775-788.

* cited by examiner

Primary Examiner — Nizal Chandrakumar
(74) Attorney, Agent, or Firm — Klauber & Jackson LLC (57) ABSTRACT Methods for treating a subject with tyrosinase-positive albinism; agents and compositions thereof for use in treating tyrosinase-positive albinism; and medicaments for treating tyrosinase-positive albinism are described herein. Such methods; agents and compositions thereof; and medicaments relate to chloroquine or rapamycin or compositions thereof and may further relate to nitisinone used in conjunction with the chloroquine or rapamycin or a composition of either of which.

5 Claims, 5 Drawing Sheets

METHODS AND AGENTS FOR TREATING TYROSINASE-POSITIVE ALBINISM

CROSS REFERENCE TO RELATED APPLICATION

This application is a National Stage Application which claims priority under 35 U.S.C. §120 from co-pending PCT Application No. PCT/US2014/037810, filed May 13, 2014, which in turn claims priority under 35 USC §119(e) from U.S. Provisional Application Ser. No. 61/822,519, filed May 13, 2013, each of which applications is herein specifically incorporated by reference in its entirety.

GOVERNMENTAL SUPPORT

The research leading to the present invention was funded in part by NIH Grant No. AR41880. The United States government has certain rights in the invention.

FIELD OF THE INVENTION

Methods for treating tyrosinase-positive albinism are described herein. In a particular embodiment, such methods comprise administering chloroquine or rapamycin or compositions thereof to a patient afflicted with tyrosinase-positive albinism. Use of chloroquine or rapamycin or compositions thereof for treating tyrosinase-positive albinism and in the manufacture of a medicament for treating tyrosinase-positive albinism are also encompassed herein.

BACKGROUND OF THE INVENTION

The citation of references herein shall not be construed as an admission that such is prior art to the present invention.

Oculocutaneous albinism (OCA) connotes a group of genetic disorders that share in common a reduced ability of melanocytes in the skin, hair and eyes and retinal pigment epithelial cells to make melanin pigment. This results in abnormalities in development of the eye, in a greatly increased risk of sun induced skin cancers and in significant diminution in quality of life. So-called "tyrosinase-negative albinism" is due to mutations in the gene encoding tyrosinase, the rate limiting enzyme involved in melanin biosynthesis, that abolish the enzyme's activity. "Tyrosinase-positive" albinism connotes the forms of oculocutaneous albinism in which tyrosinase enzyme, with the potential to be functional, is made but may be misfolded or mistrafficked, or where melanin synthesis is reduced by changes in other gene products, for example the OCA2 and OCA3 gene products. Other than sun avoidance/sun protection strategies and use of aids to improve visual acuity, no treatment is available for any form of OCA.

SUMMARY OF THE INVENTION

The present inventors have discovered certain compounds that can correct the pigmentary defect in melanocytes from mice with different forms of "tyrosinase-positive" albinism. The activity of these compounds is further enhanced by elevation of tyrosine. Exemplary such compounds identified using the screening assays described herein include chloroquine and rapamycin.

In that no treatments are available for tyrosinase-positive albinism, the identification of compounds that can correct the pigmentary defect in melanocytes derived from "tyrosinase-positive" albinism subjects presents a significant advancement for the treatment of subjects afflicted with these forms of albinism. In accordance with results presented herein, chloroquine and rapamycin have been identified as compounds that can be used to correct the pigmentary defect in melanocytes derived from "tyrosinase-positive" albinism subjects and thus, are promising therapeutic agents for intervention in tyrosinase-positive albinism. These compounds, furthermore, have the advantage of oral bioavailability and a history of safe human use.

Nitisinone, an oral drug that has as a side effect the elevation of serum tyrosine, has been used to treat mice with a mutation in the tyrosinase gene that causes a temperature sensitive enzyme that folds improperly at elevated temperatures. It has not, however, been used in non-tyrosinase associated forms of OCA. The present inventors believe that the compounds identified herein as therapeutic agents for tyrosinase-positive albinism will exhibit superior activity if combined with nitisinone. Accordingly, combinations of chloroquine and nitisinone or rapamycin and nitisinone for treating tyrosinase-positive albinism are also envisioned herein. More particularly, oral treatment of persons with OCA or women bearing fetuses with OCA using the compounds identified herein alone or in combination with compounds such as nitisinone is hereby encompassed. Compositions comprising these combinations are also encompassed herein, as are methods of treating and use of such compositions in the treatment of persons with OCA or women bearing fetuses with OCA In a particular aspect, a method for treating tyrosinase-positive albinism in a subject is presented, the method comprising administering a therapeutically effective amount of chloroquine or a composition thereof or a therapeutically effective amount of rapamycin or a composition thereof to the subject, thereby treating the subject. Also encompassed herein is a method for increasing pigmentation (in localized or systemic fashion) in a subject afflicted with tyrosinase-positive albinism, the method comprising administering a therapeutically effective amount of chloroquine or a composition thereof or a therapeutically effective amount of rapamycin or a composition thereof to the subject, thereby increasing pigmentation in the subject. In a particular embodiment, the method further comprises administering a therapeutically effective amount of nitisinone to the subject.

In a particular embodiment, the subject is a mammal. In a more particular embodiment, the mammal is a human.

In another particular embodiment, the administering is systemic or topical. Oral administration, for example, is envisioned as an exemplary approach for systemic delivery.

In a further aspect, a composition comprising a therapeutically effective amount of chloroquine and a therapeutically effective amount of nitisinone for the treatment of tyrosinase-positive albinism or for increasing pigmentation (in localized or systemic fashion) in subject afflicted with tyrosinase-positive albinism is presented.

In a still further aspect, a composition comprising a therapeutically effective amount of rapamycin and a therapeutically effective amount of nitisinone for the treatment of tyrosinase-positive albinism or for increasing pigmentation (in localized or systemic fashion) in subject afflicted with tyrosinase-positive albinism is presented.

In another aspect, use of chloroquine or a composition thereof or rapamycin or a composition thereof for the manufacture of a medicament for treating tyrosinase-positive albinism in a subject is envisioned, wherein the medicament is prepared to be administrable in a dosage regimen whereby chloroquine or a composition thereof or rapamycin or a composition thereof is delivered in a therapeutically effective amount to the subject. The medicament may optionally further comprise nitisinone in a therapeutically effective amount. As described herein, the subject may be a mammal and, more particularly, a human. The medicament may be manufactured to be administrable systemically (e.g., orally or intravenously) or topically.

In yet another aspect, chloroquine or a composition thereof or rapamycin or a composition thereof is envisioned for use in the treatment of tyrosinase-positive albinism in a subject, wherein the chloroquine or a composition thereof or rapamycin or a composition thereof is administered in a therapeutically effective amount to the subject. Nitisinone is also envisioned herein for use, in conjunction with chloroquine or a composition thereof or rapamycin or a composition thereof, in the treatment of tyrosinase-positive albinism in a subject, wherein the nitisinone is administered in a therapeutically effective amount to the subject. The subject may be a mammal and, more particularly, may be a human. The chloroquine or a composition thereof or rapamycin or a composition thereof, without or with nitisinone, for use as described herein may be administered systemically (e.g., orally or intravenously) or topically.

Other objects and advantages will become apparent to those skilled in the art from a review of the ensuing detailed description, which proceeds with reference to the following illustrative drawings, and the attendant claims.

DETAILED DESCRIPTION

A chemical library screen was undertaken in order to identify agents that increase pigmentation in mouse melanocytes that lack expression of the Oca2 protein (Oca2-null). These cells represent an animal model for the human disorder OCA2. The present inventors screened two chemicals libraries of over 2000 compounds that represent many approved drugs and natural products and identified multiple small molecules that increase the pigmentation of Oca2-null melanocytes. Surprisingly, a majority of agents that increase pigmentation in mutant melanocytes had been identified previously by the present inventors as compounds that reduce pigmentation in normal melanocytes. For example, chloroquine was one of several quinolines found to decrease pigmentation in normal melanocytes (Ni-Komatsu, et al. (2008). Mol Pharmacol 74(6): 1576-1586.), but shown herein to increase pigmentation in Oca2-null, as shown in FIG. 1, and in Oca3-null melanocytes, as shown in FIG. 2.

Figure 1:
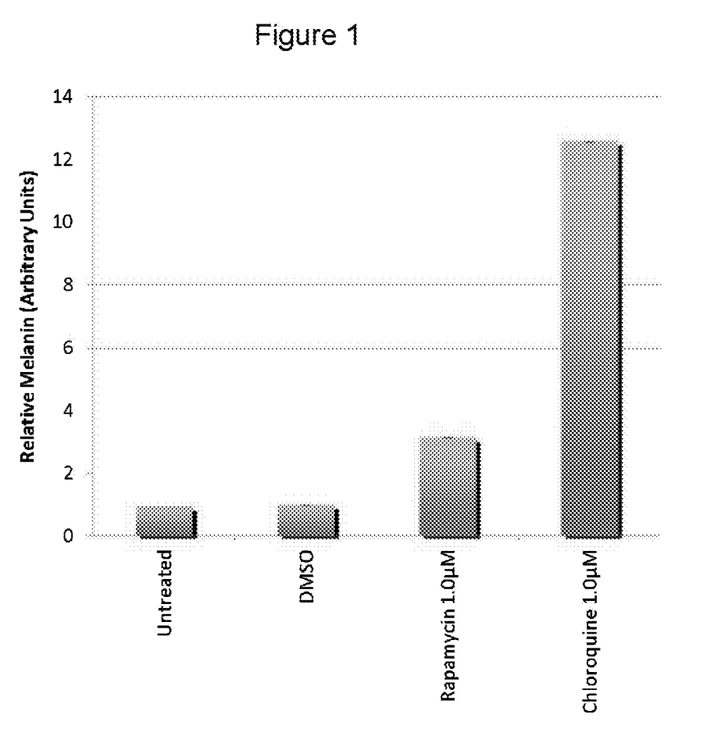
FIG. 1 shows a histogram plot of melanin levels in melanocytes derived from Oca2-null (OCA2) melanocytes which have been treated with the indicated compounds.
Figure 2:
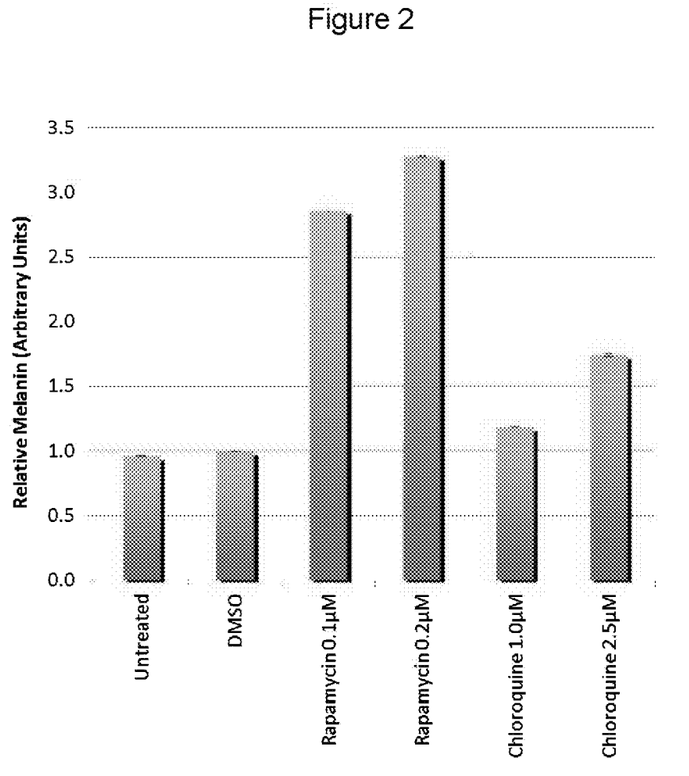
FIG. 2 shows a histogram plot of melanin levels in melanocytes derived from Oca3-null (OCA3) melanocytes which have been treated with the indicated compounds.

A second agent found to increase pigmentation in Oca2-null and Oca3-null cells is rapamycin as shown in FIGS. 1 and 2. While rapamycin has been reported previously to increase pigmentation in melanoma cells by upregulating expression of tyrosinase, these findings do not suggest that it should be considered a promising agent for increasing pigmentation in OCA2-null cells, firstly because the present inventors have shown that Oca2-null cells express higher levels of tyrosinase than wildtype cells, thus agents that increase tyrosinase expression in Oca2-null cells are not expected to correct the hypopigmentation defect of these cells and secondly because the majority of agents identified in the screen described herein increase pigmentation of mutant cells, but cause a decrease in pigmentation in normal melanocytes.

Given that tyrosinase retention in the endoplasmic reticulum is a common feature of both OCA2 and OCA3 (caused by mutations in the TYRP1 gene), the present inventors also tested the effects of rapamycin and chloroquine on melanocytes established from the murine OCA3 model. As indicated herein above, both agents were found to increase pigmentation in Oca3-null cells. See FIG. 2.

It is noteworthy that agents that promote melanogenesis in wildtype melanocytes cannot reasonably be expected to increase pigmentation in Oca2-null melanocytes. A common mechanism by which agents increase pigmentation in wildtype melanocytes is by promoting tyrosinase expression. In order to also promote an increase in pigmentation, these agents require efficient maturation and delivery of tyrosinase to the melanosome where melanin is synthesized. These processes are disrupted in Oca2-null melanocytes. Furthermore, Oca2-null cells already express elevated levels of tyrosinase as compared to wildtype melanocytes, but reduced rates of maturation and trafficking of tyrosinase in the Oca2-null cells results in hypopigmentation. To illustrate this, the present inventors tested the effects of forskolin and 3-isobutyl-1-methylxanthine (IBMX), agents known to increase pigmentation in wildtype melanocytes. The agents were effective in increasing the melanin content of wildtype (WT) melanocytes, but not Oca2-null (OCA2) melanocytes. Bafilomycin, which is highly toxic to wildtype melanocytes, even at nanomolar concentrations, increased the melanin content of Oca2-null melanocytes with much less accompanying toxicity. See, for example, FIG. 3.

The present inventors have, furthermore, previously shown that the tricyclic antidepressants (TCAs) significantly reduce the levels of melanin produced in wildtype melanocytes (Ni-Komatsu & Orlow. J Invest Dermatol. 2008, 128(5):1236-47). See, for example, FIG. 4.

These same agents, however, increase pigmentation in melanocytes that lack functional Oca2 protein. See, for example, FIG. 5.

The results presented herein, therefore, underscore that it is not possible to predict how a compound or agent will influence melanin levels in a given cell, particularly those derived from a subject afflicted with a tyrosinase-positive form of albinism.

Agents/Compounds

The structure of chloroquine is presented below:

Chloroquine

The systematic (IUPAC) name is (RS)—N'-(7-chloroquinolin-4-yl)-N,N-diethyl-pentane-1,4-diamine. Additional compounds related to chloroquine are also envisioned as agents having applicability to or with methods, uses and medicaments described herein, structures for which are presented in U.S. Patent Application Publication Number 2009/0298868, the entire content of which is incorporated herein by reference. Screening assays to identify agents that modify or mimic P protein function in melanocytes are, furthermore, described in U.S. Pat. No. 7,378,232, the entire content of which is incorporated herein by reference.

The structure of rapamycin is presented below:

Rapamycin (also referred to as Sirolimus) is a macrolide compound that selectively blocks transcriptional activation of cytokines and thus, inhibits cytokine production. It is a potent immunosuppressant and exhibits both antifungal and antineoplastic properties. Hydroxyesters of rapamycin are known and described in, for example, U.S. RE 44,768 (the entire content of which is incorporated herein by reference) and are envisioned for use in accordance with methods, uses, and medicaments described herein.

Methodological Details Pertaining to the Drawings

Methodology for FIG. 1:

Oca2-null cells were plated in 60 mm dishes for 24 hours followed by dosing with the indicated compounds. DMSO was used as a vehicle control (to establish the baseline for comparison). Cells were harvested after 5 days. Melanocytes were harvested in extraction buffer (50 mM Tris pH7.5, 2 mM EDTA, 150 mM NaCl) containing 1% Triton X-100 and protease inhibitors (Complete, Roche Indianapolis, Ind.) following two washes with 1× phosphate buffered saline (PBS). The lysate was centrifuged for 30 min at 13,000 rpm in a microfuge. The supernatant was removed and the protein concentration determined using a protein assay kit (BioRad, Richmond, Calif.). Three hundred μl of ethanol:ether (1:1) were added to the pellet, which was then vortexed. After incubation at room temperature for 10 min, the solvent was removed (leaving the melanin behind) and the ethanol:ether wash repeated without vortexing. The melanin was then dissolved in 2 N NaOH, 20% DMSO at 60-70° C. The optical density was determined at 490 nm. The value was normalized to protein concentration in the supernatant and expressed as a ratio of the melanin in the vehicle treated cells.

Methodology for FIG. 2:

Oca3-null melanocytes were seeded in six-well plates in triplicate. After 24 hours, each cell line was treated with vehicle, chloroquine or rapamycin. Plates were incubated for 72 hours. Melanocytes were harvested and a melanin assay performed as described above.

Figure 3:
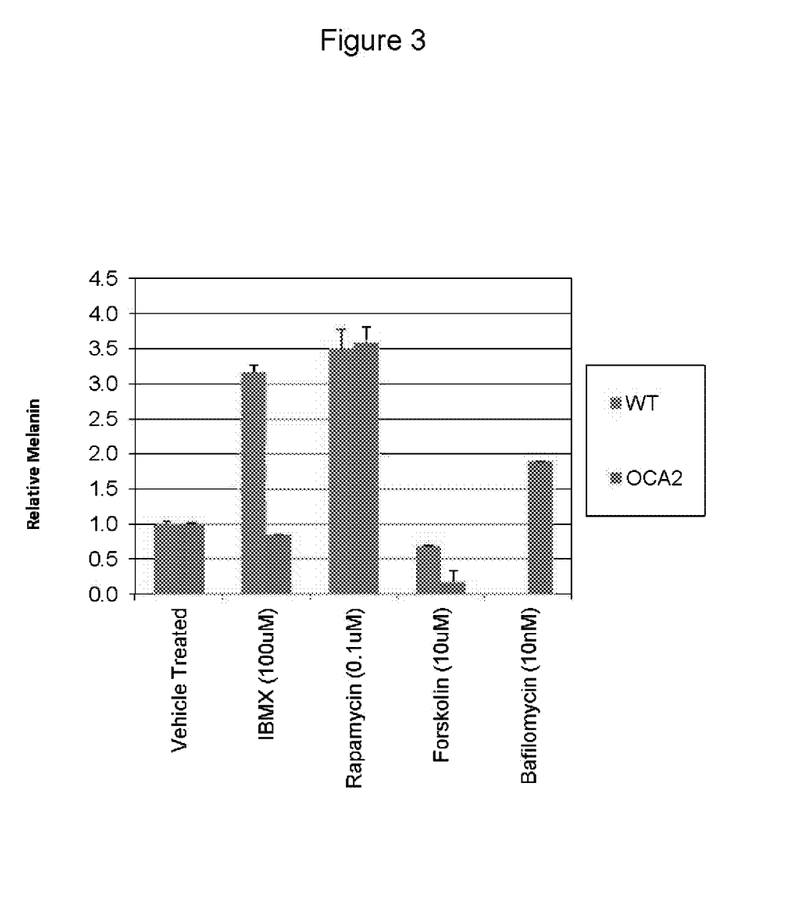
FIG. 3 shows a histogram plot of melanin levels in melanocytes derived from wildtype (WT) and Oca-2-null (OCA2) melanocytes which have been treated with the indicated compounds.

Methodology for FIG. 3:

Cells were seeded in six-well plates in triplicate. After 24 hours, each cell line was treated with IBMX, forskolin or rapamycin, in addition, Oca2-null melanocytes were treated with bafilomycin. Plates were incubated for 72 hours. Melanocytes were harvested and a melanin assay performed as described above.

Figure 4:
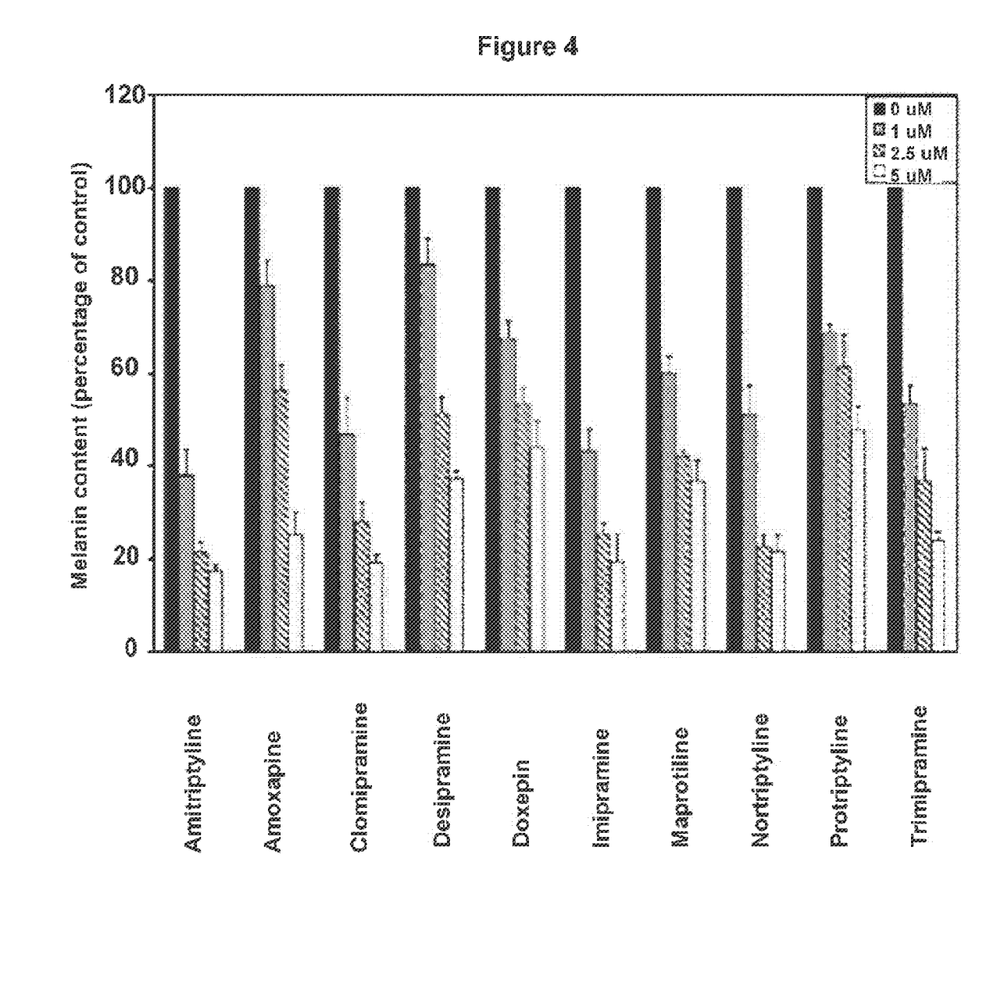
FIG. 4 shows a histogram plot of melanin levels in wildtype cells treated with the indicated compounds.

Methodology for FIG. 4:

Wildtype cells were plated in 24-well plates for 24 hours followed by dosing with the indicated compounds. DMSO was used as a vehicle control. Cells were harvested after 3 days and a melanin assay was performed as described above.

Figure 5:
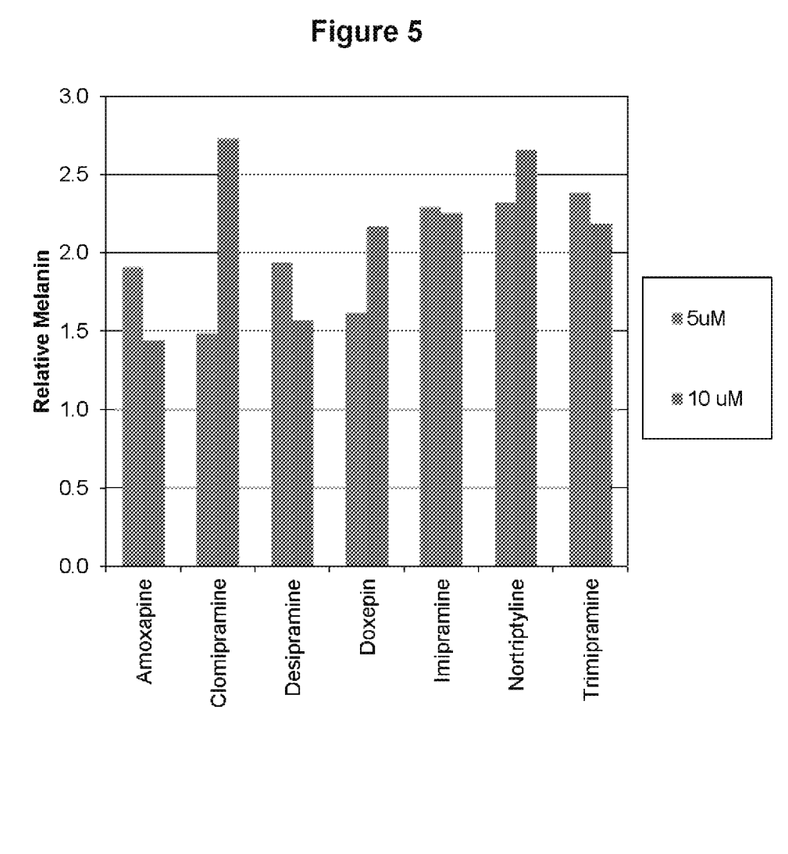
FIG. 5 shows a histogram plot of melanin levels in Oca2-null cells treated with the indicated compounds.

Methodology for FIG. 5:

Oca2-null cells were plated in 60 mm dishes for 24 hours followed by dosing with the indicated compounds. DMSO was used as a vehicle control. Cells were harvested after 7 days and a melanin assay was performed as described above.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

The term "subject" as used herein may refer to a mammal (e.g., a mouse, rat, cat, dog, farm animal, or primate). In a more particular embodiment, the mammal is a human.

The term 'treating' or 'treatment' of any disease or infection refers, in one embodiment, to ameliorating the disease or infection (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically (e.g., stabilization of a physical parameter), or both. In a further embodiment, 'treating' or 'treatment' relates to slowing the progression of a disease.

The phrase "pharmaceutically acceptable" refers to molecular entities and compositions that are physiologically tolerable and do not typically produce an allergic or similar untoward reaction, such as gastric upset, dizziness and the like, when administered to a human.

Agents, compounds, and compositions of the present invention may be administered to a patient in need of treatment via any suitable route, including by intravenous, intraperitoneal, intramuscular injection, or orally. The precise dose will depend upon a number of factors, including whether the agents, compounds, or compositions are for treatment or for prevention. The dosage or dosing regime of an adult patient may be proportionally adjusted for children and infants, and also adjusted for other administration or other formats, in proportion for example to molecular weight or immune response. Administration or treatments may be repeated at appropriate intervals, at the discretion of the physician.

Agents and compounds described herein are generally administered in the form of a pharmaceutical composition, which may comprise at least one component in addition to the agents and compounds. Pharmaceutical compositions according to the present invention, and for use in accordance with the present invention, may comprise, in addition to active ingredient, a pharmaceutically acceptable excipient, carrier, buffer, stabiliser or other materials known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

The preparation of therapeutic compositions which contain agents or compounds as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

Agents or compounds can be formulated into a therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The agent or compound containing compositions are conventionally administered intramuscularly, intravenously, as by injection of a unit dose, or orally, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of activation and immune response desired. Precise amounts of active ingredient required to be administered depend on the judgment of the practitioner and are peculiar to each individual. Suitable regimens for initial administration and follow on administration are also variable, and may include an initial administration followed by repeated doses at appropriate intervals by a subsequent injection or other administration.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, and Lactated Ringer's Injection. Preservatives, stabilizers, buffers, antioxidants and/or other additives may be included, as required.

For oral administration, chloroquine is administered in the form of a tablet or capsule or the like and has properties suitable to this mode of administration as understood by those of skill in the art. In accordance with various therapeutic applications and clinical trials, chloroquine is administered to a human subject in need thereof orally at a dose ranging from about 50-350 mg/day. In a more particular embodiment, chloroquine is administered orally to a human subject in need thereof at a dose ranging from about 100-250 mg/day. In a more particular embodiment, chloroquine is administered orally to a human subject in need thereof at a dose of about 250 mg/day. See also United States Clinical Trial Nos. NCT02004314 and NCT00969306, the entire content of each of which is incorporated herein by reference.

For oral administration, rapamycin is administered in the form of a tablet or capsule or the like and has properties suitable to this mode of administration as understood by those of skill in the art. In accordance with various therapeutic applications, rapamycin is administered to a human subject in need thereof orally at a dose of about 3 mg/m$^2$ load for a human subject of <40 kg or about 2-20 mg (in a particular embodiment, e.g., 6-15 mg, 6, or 15 mg) load for a human subject of ≥40 kg. In another embodiment, rapamycin is administered at about 1-5 mg/day per oral (PO) if a human subject is >40 kg (in a particular embodiment, e.g., 2 or 5 mg/day) and 1 mg/m$^2$/day if the human subject is <40 kg on day 2 of treatment and thereafter.

Example 1

Methodology

The present inventors utilized the chemical genetics approach described herein to identify compounds that can be used to reverse the diminished pigmentation in Oca2-null cells. To this end, they first developed a 96-well assay system for rapid compound screening. Melanocytes were cultured in a 96-well plate in the presence of test compounds. Melanin content was determined by replacing the culture medium with PBS and measuring absorbance at 490 nm. As the number of cells per well significantly impacts the melanin content per well, an MTS cell proliferation assay was performed following the absorbance assay to determine the relative number of cells. The assay was validated using bafilomycin A1, an ATPase inhibitor that reverses the pigmentation phenotype of OCA2-null cells.

Following validation of their assay system, the present inventors performed a screen, treating Oca2-null cells with library compounds at concentrations of 5 and/or 1 µM. Each plate included untreated Oca2-null cells as negative controls and cells treated with bafilomycin A1 as positive controls. Compounds identified as potential hits were then re-screened to verify their ability to promote melanin synthesis in cells lacking functional Oca2 protein.

Selected compounds identified in the screen were tested using a traditional melanin assay in order to verify the findings of the screen. Following 3 (normal melanocytes) or 5 (mutant melanocytes) days of treatment, melanocytes were harvested in extraction buffer (50 mM Tris pH7.5, 2 mM EDTA, 150 mM NaCl) containing 1% Triton X-100 and protease inhibitors (Complete, Roche Indianapolis, Ind.) following two washes with 1× phosphate buffered saline (PBS). The lysate was centrifuged for 30 min at 13,000 rpm in a microfuge. The supernatant was removed and the protein concentration determined using a protein assay kit (BioRad, Richmond, Calif.). Three hundred μl of ethanol:ether (1:1) were added to the pellet, which was then vortexed. After incubation at room temperature for 10 min, the solvent was removed (leaving the melanin behind) and the ethanol:ether wash repeated without vortexing. The melanin was then dissolved in 2 N NaOH, 20% DMSO at 60-70° C. The optical density was determined at 490 nm. The value was normalized to protein concentration in the supernatant and expressed as a ratio of the melanin in the untreated cells.

While certain of the particular embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating tyrosinase-positive albinism in a subject, the method comprising administering a therapeutically effective amount of chloroquine or a composition thereof to the subject.

2. The method of claim 1, further comprising administering a therapeutically effective amount of nitisinone to the subject.

3. The method of claim 1, wherein the subject is a mammal.

4. The method of claim 3, wherein the mammal is a human.

5. The method of claim 1, wherein the administering is systemic or topical.

* * * * *

UNITED STATES PATENT AND TRADEMARK OFFICE
CERTIFICATE OF CORRECTION

PATENT NO. : 9,717,722 B2
APPLICATION NO. : 14/890696
DATED : August 1, 2017
INVENTOR(S) : Seth J. Orlow et al.

It is certified that error appears in the above-identified patent and that said Letters Patent is hereby corrected as shown below:

In the Specification

At Column 1, Lines 17-19, replace:
"The research leading to the present invention was funded in part by NIH Grant No. AR41880. The United States government has certain rights in the invention."

With:
--This invention was made with government support under grant number AR041880 awarded by the National Institutes of Health. The government has certain rights in the invention.--

Signed and Sealed this
Third Day of September, 2019

Andrei Iancu
*Director of the United States Patent and Trademark Office*